United States Patent
Jung et al.

(10) Patent No.: US 10,980,767 B2
(45) Date of Patent: Apr. 20, 2021

(54) ESTROGEN RECEPTOR LIGANDS, COMPOSITIONS AND METHODS RELATED THERETO

(71) Applicant: The Regents of the University of California, Oakland, CA (US)

(72) Inventors: Michael E. Jung, Los Angeles, CA (US); Rhonda R. Voskuhl, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/331,670

(22) PCT Filed: Sep. 8, 2017

(86) PCT No.: PCT/US2017/050588
§ 371 (c)(1),
(2) Date: Mar. 8, 2019

(87) PCT Pub. No.: WO2018/049094
PCT Pub. Date: Mar. 15, 2018

(65) Prior Publication Data
US 2019/0192476 A1    Jun. 27, 2019

Related U.S. Application Data

(60) Provisional application No. 62/516,177, filed on Jun. 7, 2017, provisional application No. 62/393,430, filed on Sep. 12, 2016, provisional application No. 62/385,725, filed on Sep. 9, 2016.

(51) Int. Cl.
| | |
|---|---|
| *A61K 31/277* | (2006.01) |
| *A61P 25/14* | (2006.01) |
| *A61P 25/28* | (2006.01) |
| *A61P 25/16* | (2006.01) |
| *A61K 45/06* | (2006.01) |

(52) U.S. Cl.
CPC ............ *A61K 31/277* (2013.01); *A61K 45/06* (2013.01); *A61P 25/14* (2018.01); *A61P 25/16* (2018.01); *A61P 25/28* (2018.01)

(58) Field of Classification Search
CPC .................................................... A61K 31/277
USPC ......................................................... 514/521
See application file for complete search history.

(56) References Cited

U.S. PATENT DOCUMENTS

2011/0256096 A1    10/2011    Voskuhl et al.

OTHER PUBLICATIONS

Kumar et al., "Estrogen receptor β ligand therapy activates PI3K/Akt/mTOR signaling in oligodendrocytes and promotes remyelination in a mouse model of multiple sclerosis", Neurobiology of Disease, vol. 56, pp. 131-144 (2013).*
Carroll et al., "Diarylpropionitrile (DPN) enantiomers: synthesis and evaluation of estrogen receptor β-selective ligands," J Med Chem, 55(1):528-537 (2011).
International Search Report and Written Opinion for International Application No. PCT/US2017/050588 dated Dec. 28, 2017.
Kumar et al., "Estrogen receptor β ligand therapy activates PI3K/Akt/mTOR signaling in oligodendrocytes and promotes remyelination in a mouse model of multiple sclerosis," Neurobiol Dis, 56:131-144 (2013).
Rautio et al., "Prodrugs: design and clinical applications," Nat Rev Drug Discov, 7(3):255-270 (2008).
Supplementary European Search Report for EP Application No. 17849572 dated Feb. 5, 2020.

* cited by examiner

*Primary Examiner* — Kevin E Weddington
(74) *Attorney, Agent, or Firm* — Foley Hoag LLP; David P. Halstead; Alexander J. Chatterley

(57) ABSTRACT

Provided are compounds and methods for treating neurodegenerative diseases and conditions, such as multiple sclerosis, using an estrogen receptor-β ligand (ERβ ligand).

19 Claims, 7 Drawing Sheets

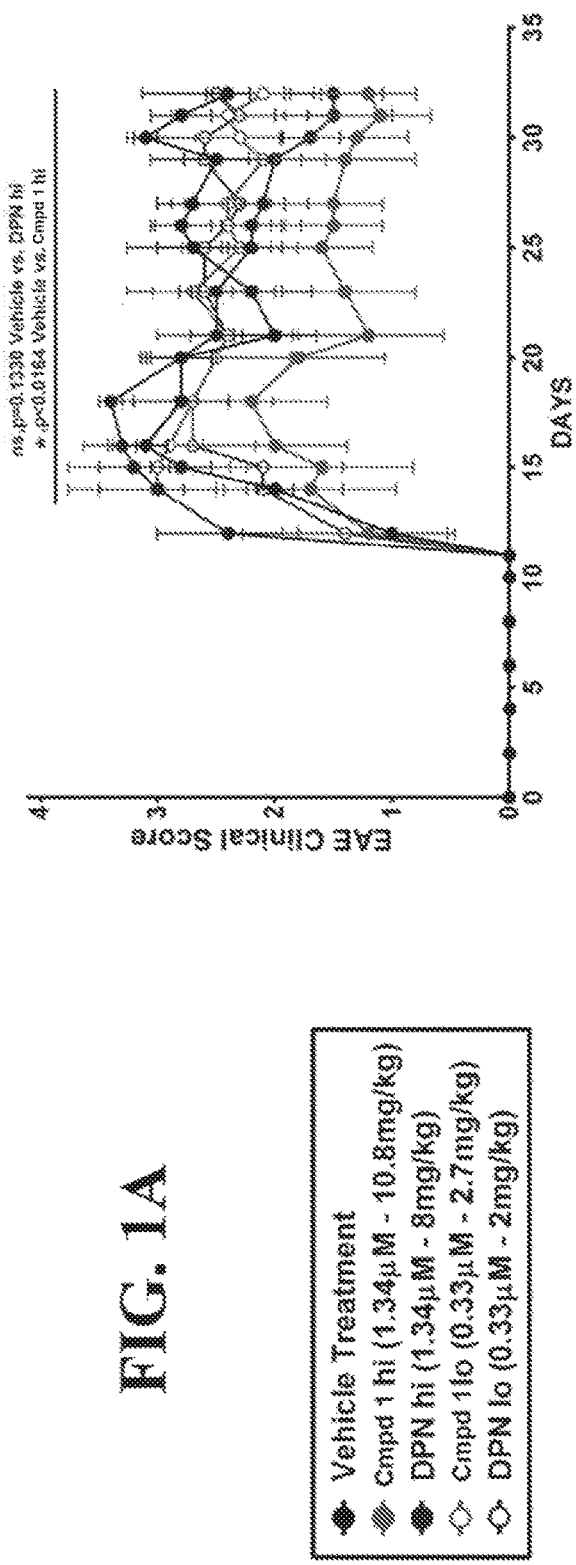
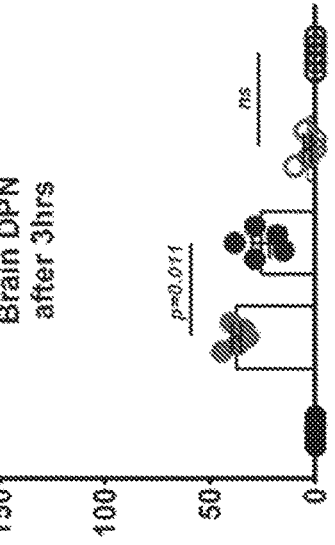
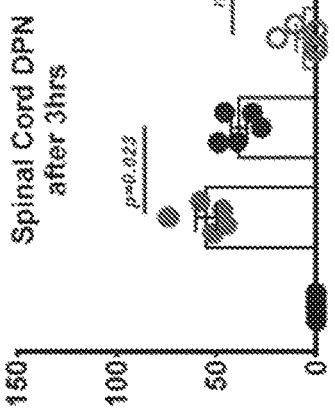
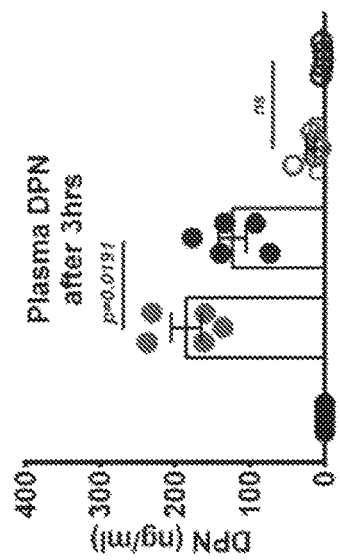

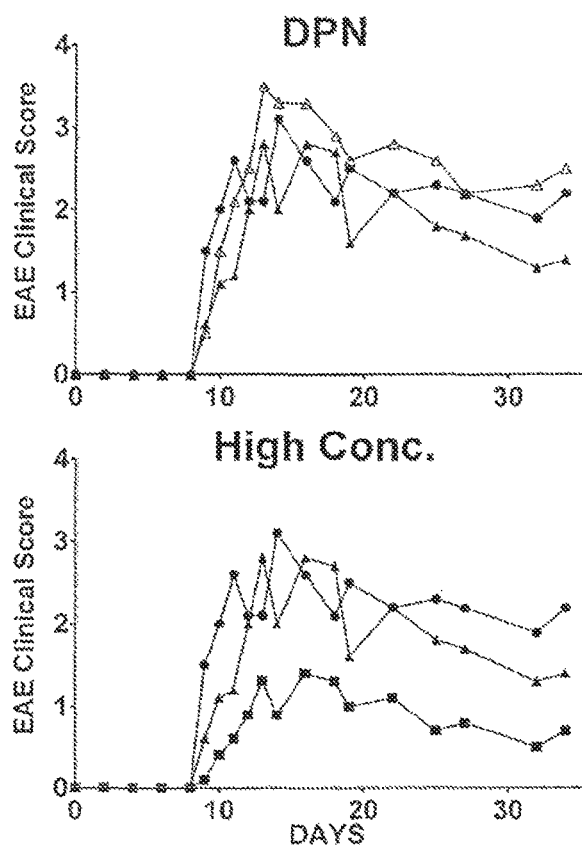
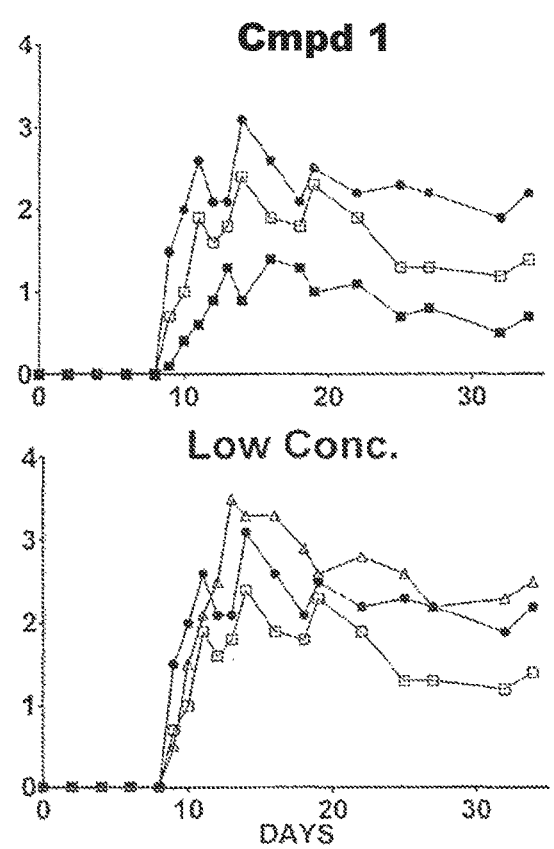
Fig. 3A  Fig. 3B
Fig. 3C  Fig. 3D

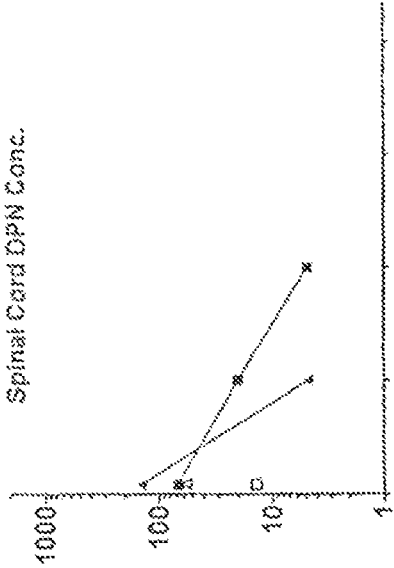
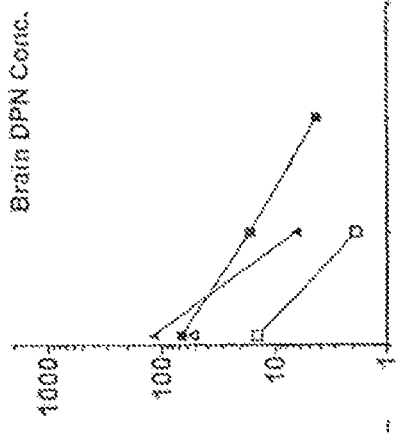
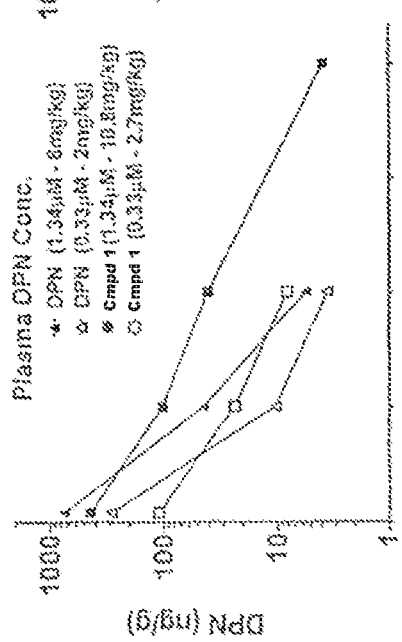

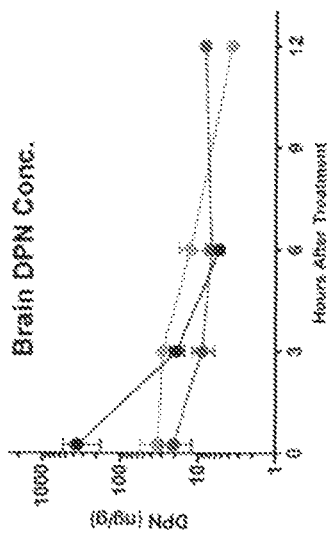
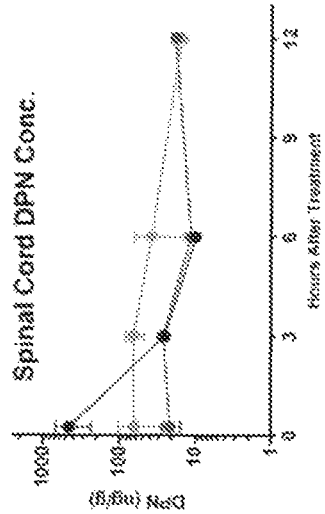
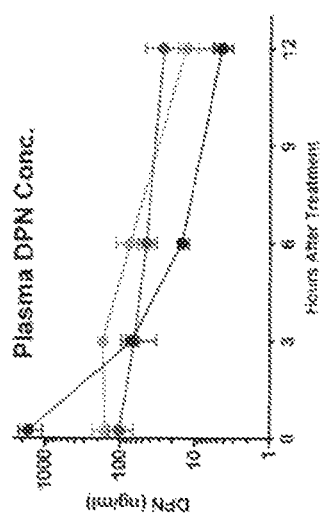

ESTROGEN RECEPTOR LIGANDS, COMPOSITIONS AND METHODS RELATED THERETO

RELATED APPLICATION

This application is a national-stage filing under 35 U.S.C. 371 of International Application PCT/US2017/050588, filed May 26, 2017, which claims the benefit of priority to U.S. provisional patent application Ser. No. 62/385,725, filed Sep. 9, 2016; U.S. provisional patent application Ser. No. 62/393,430, filed Sep. 12, 2016; and U.S. provisional patent application Ser. No. 62/516,177, filed Jun. 7, 2017, the contents of each of which are incorporated by reference in their entirety.

BACKGROUND

Multiple sclerosis (MS) is a chronic, often debilitating neurodegenerative disease affecting the central nervous system (brain and spinal cord). MS affects more than 1 million people worldwide and is the most common neurological disease among young adults, particularly women. The exact cause of MS is still unknown. MS is an autoimmune disease in which myelin sheaths surrounding neuronal axons are destroyed. This condition can cause weakness, impaired vision, loss of balance, and poor muscle coordination.

MS takes several forms, with new symptoms either occurring in isolated attacks (relapsing forms) or building up over time (progressive forms). Between attacks, symptoms may disappear completely; however, permanent neurological problems often occur, especially as the disease advances.

In 1996, the United States National Multiple Sclerosis Society described four clinical subtypes of MS: (i) relapsing-remitting; (ii) secondary-progressive; (iii) primary-progressive; and (iv) progressive-relapsing.

Relapsing-remitting MS is characterized by unpredictable relapses followed by periods of months to years of relative quiet (remission) with no new signs of disease activity. Deficits that occur during attacks may either resolve or leave sequelae, the latter in about 40% of attacks and being more common the longer a person has had the disease. This describes the initial course of 80% of individuals with MS. When deficits always resolve between attacks, this is sometimes referred to as benign MS, although people will still build up some degree of disability in the long term. On the other hand, the term malignant multiple sclerosis is used to describe people with MS having reached significant level of disability in a short period of time. The relapsing-remitting subtype usually begins with a clinically isolated syndrome (CIS). In CIS, a person has an attack suggestive of demyelination but does not fulfill the criteria for multiple sclerosis; about 30% to about 70% of persons experiencing CIS go on to develop MS.

Secondary-progressive MS occurs in around 65% of those with initial relapsing-remitting MS, who eventually have progressive neurologic decline between acute attacks without any definite periods of remission. Occasional relapses and minor remissions may appear. The median length of time between disease onset and conversion from relapsing-remitting to secondary progressive MS is about 19 years.

Primary-progressive MS occurs in approximately 10-20% of individuals, with no remission after the initial symptoms. It is characterized by progression of disability from onset, with no, or only occasional and minor, remissions and improvements. The usual age of onset for the primary progressive subtype is later than of the relapsing-remitting subtype, but similar to the age that secondary-progressive MS usually begins in relapsing-remitting MS, around 40 years of age.

Progressive-relapsing MS describes those individuals who, from onset, have a steady neurologic decline but also have clear superimposed attacks. This is the least common of all subtypes.

Current MS treatments have immunomodulatory effects and reduce relapse rates in MS patients, but have only modest effects on disability progression. The following agents are approved by the U.S. Food and Drug Administration (FDA) to reduce disease activity and disease progression for many people with relapsing forms of MS, including relapsing-remitting MS, as well as secondary-progressive and progressive-relapsing MS in those people who continue to have relapses: dimethyl fumarate (Tecfidera®; BG-12), fingolimod (Gilenya®), glatiramer acetate (Copaxone®), interferon beta-1a (Avonex® and Rebif®), interferon beta-1b (Betaseron® and Extavia®), mitoxantrone (Novantrone®), natalizumab (Tysabri®), and teriflunomide (Aubagio®). However, many of these therapies fail to successfully treat all patients or all symptoms in treated patients, and many of these therapies are associated with undesirable side effects.

Compounds that bind to estrogen receptor-α have shown neuroprotective efficacy, but also produce undesirable levels of side effects. Estriol is known to preferentially bind to estrogen receptor-β (ERβ) and has a reduced level of adverse side effects. Improvements upon estriol with novel ERβ ligands would provide more efficacious and well-tolerated therapies for halting disability progression in patients with MS and other neurodegenerative diseases or conditions.

SUMMARY

Disclosed herein are methods of treating a neurodegenerative disease or condition comprising administering an ERβ ligand to a subject in need thereof. In certain embodiments, the ERβ ligand is a compound of Formula (I)

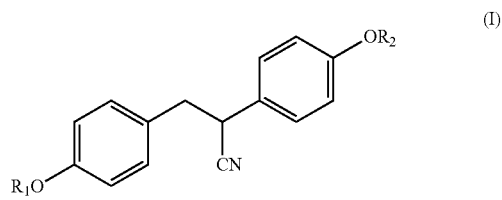

wherein
$R_1$ and $R_2$ are each independently —C(O)—$R_3$; and
$R_3$ is selected from alkyl, alkoxy, alkoxyalkyl, aryloxyalkyl, cycloalkyl, cycloalkylalkyl, aryl, aralkyl, heterocyclyl, heterocyclylalkyl, heteroaryl, and heteroarylalkyl.

In certain preferred embodiments, $R_1$ and $R_2$ are each —C(O)—$R_3$, and each $R_3$ is selected from alkyl, aryl and aralkyl. In such embodiments, $R_1$ and $R_2$ may be the same or different, but for ease of preparation are preferably the same.

In certain embodiments, the ERβ ligand is Compound 1, or pharmaceutically acceptable salts of any of the foregoing, and any combination thereof.

In certain embodiments, the compound of Formula (I) is Compound 1:

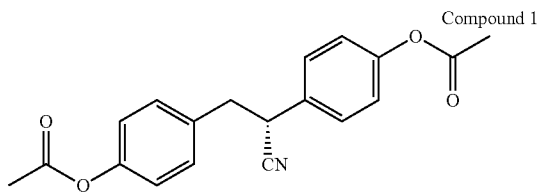 [SMILES: CC(=O)Oc1ccc(C[C@@H](C#N)c2ccc(OC(C)=O)cc2)cc1]

Compound 1

In certain embodiments, the multiple sclerosis is relapsing-remitting multiple sclerosis.

In certain embodiments, the multiple sclerosis is secondary-progressive multiple sclerosis.

In certain embodiments, the multiple sclerosis is primary-progressive multiple sclerosis.

In certain embodiments, the multiple sclerosis is progressive-relapsing multiple sclerosis.

In certain embodiments, the multiple sclerosis is clinically isolated syndrome (CIS).

In certain embodiments, the method further comprises administering to the subject an immunotherapeutic agent, wherein the immunotherapeutic agent is selected from interferon-beta 1a, interferon-beta 1b, glatiramer acetate, natalizumab, mitoxantrone, fingolimod, teriflunomide, and dimethyl fumarate.

In certain embodiments, the subject is being treated with an immunotherapeutic agent, yet experiencing a relapse and/or progression of the multiple sclerosis.

Although the methods disclosed throughout the specification and claims are useful for treating multiple sclerosis in its various forms and stages, these methods can also be applied the treatment of other neurodegenerative diseases and conditions, such as, but not limited to, Alzheimer's disease, Mild Cognitive Impairment (MCI), cognitive impairment with menopause (natural aging or surgical), Parkinson's disease, stroke, amyotrophic lateral sclerosis, cerebellar ataxia, frontotemporal dementia, prion disease, Huntington's Disease, cerebral ischemia, idiopathic Morbus Parkinson, Parkinson syndrome, Morbus Alzheimers, cerebral dementia syndrome, infection-induced neurodegeneration disorders (e.g., AIDS-encephalopathy, Creutzfeld-Jakob disease, encephalopathies induced by rubiola, herpes viruses and borrelioses), metabolic-toxic neurodegenerative disorders (such as hepatic-, alcoholic-, hypoxic-, hypo- or hyperglycemically-induced encephalopathies), encephalopathies induced by solvents or pharmaceuticals, degenerative retina disorders, trauma-induced brain damage, trauma-induced bone marrow damage, cerebral hyperexcitability symptoms, cerebral hyperexcitability states (e.g., of varying origin, such as after the addition of and/or withdrawal of medicaments, toxins, noxae and drugs), neurodegenerative syndromes of the peripheral nervous system, peripheral nerve injury, and spinal cord injury. In certain preferred embodiments, the neurodegenerative disease is multiple sclerosis.

In certain embodiments, the method is a method for slowing, halting, or reversing progression of a cognitive or physical disability in a subject with a neurodegenerative disease, comprising identifying a subject who has experienced progression of a cognitive or physical disability and initiating treatment of the subject by a method as described herein. In certain embodiments, the method further comprises testing the severity of the subject's cognitive or physical disability to determine a score representative of the state of the subject's cognitive or physical disability after receiving the treatment for at least about six months, and, optionally, comparing the score to a score determined for the subject prior to or at about the time of initiating the treatment.

In other aspects, the invention relates to compounds for use in treating neurodegenerative diseases according to any of the various methods disclosed herein, and use of compounds in the manufacture of medicaments for carrying out any of the various methods disclosed herein.

BRIEF DESCRIPTION OF THE DRAWINGS

FIG. 1A is a graph of active EAE clinical scores during days of treatment with DPN or Compound 1. FIG. 1B is a graph of DPN concentration in plasma 3 hours after the end of disease. FIG. 1C is a graph of DPN concentration in spinal cord tissue 3 hours after the end of disease. FIG. 1D is a graph of DPN concentration in brain tissue 3 hours after the end of disease.

FIG. 3A is a graph of EAE clinical score during days of treatment with DPN at high and low doses. FIG. 3B is a graph of EAE clinical score during days of treatment with Compound 1 at high and low doses. FIG. 3C is a graph of EAE clinical score during days of treatment with both DPN and Compound 1 at the high dose. FIG. 3D is a graph of EAE clinical score during days of treatment with both DPN and Compound 1 at the low dose.

FIG. 4A is a graph of DPN concentration over time in plasma using DPN and Compound 1 at high and low doses. FIG. 4B is a graph of DPN concentration over time in brain tissue using DPN and Compound 1 at high and low doses. FIG. 4C is a graph of DPN concentration over time in spinal cord tissue using DPN and Compound 1 at high and low doses.

FIG. 7A is a graph of DPN concentration over time in plasma using DPN, Compound 1 and Compound 2. FIG. 7B is a graph of DPN concentration over time in brain tissue using DPN, Compound 1 and Compound 2. FIG. 7C is a graph of DPN concentration over time in spinal cord tissue using DPN, Compound 1 and Compound 2.

DETAILED DESCRIPTION

Figures 2A, 2B:
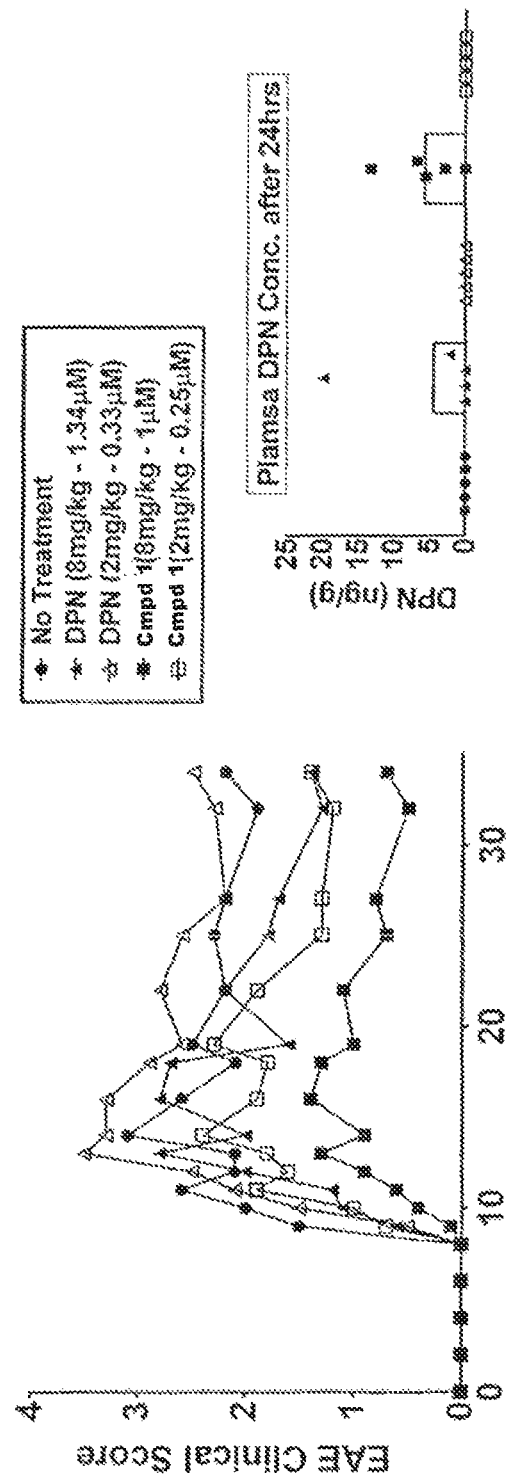
FIG. 2A is a graph of adoptive EAE clinical scores during days of treatment with DPN or Compound 1 at a high or low dose for each compound.
FIG. 2B shows the plasma concentration of DPN for each treatment cohort after 24 hrs.

Multiple sclerosis (MS) is an autoimmune disease characterized by inflammation and demyelination of the central nervous system (CNS). Approximately 50% of people diagnosed with multiple sclerosis (MS) will develop problems with cognition. Currently, there are no FDA-approved treatments targeting cognitive function in MS. The most widely used animal model for MS is experimental autoimmune encephalomyelitis (EAE). Treatment with estrogens or estrogen receptor (ER) specific-ligands in EAE are neuroprotective. ERα-ligand treatment mediates protection in EAE by acting on the peripheral immune system and astrocytes in the CNS. However, binding to ERα in uterus and breast can lead to adverse off-target effects, limiting dose and duration of usage, or requiring administration of additional therapeutic agents to attenuate the effects. Alternatively, estriol, which binds preferably to ERβ over ERα, has few side effects, and estriol treatment reduced relapses in MS patients in a phase 2 clinical trial. It also reduced fatigue in this trial, and higher estriol levels were associated with improved cognitive test performance. Finally, cortical gray matter atrophy was spared in administering estriol as compared to placebo treated MS patients. Provided herein are methods of treating MS using ERβ ligands. The efficacy of these methods has been demonstrated in an art-recognized pre-clinical model of MS known as experimental autoimmune encephalomyelitis (EAE). In certain embodiments, the disclosed methods correlate to the clinical outcomes of known treatments of MS with estriol in regards to ERβ-mediated properties.

One such known treatment of EAE is diarylpropionitrile (DPN), a generic ERβ-ligand. See, e.g., US2011/0236350 and US2011/0256096, incorporated herein by reference in their entirety.

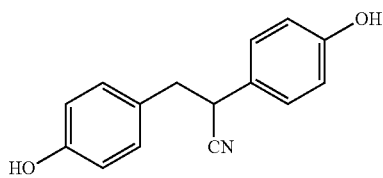 [SMILES: N#CC(Cc1ccc(O)cc1)c1ccc(O)cc1]

DPN (2,3-bis(4-hydroxyphenyl)propanenitrile)

DPN reduces clinical EAE disease severity and provides clinical disease protection by reducing demyelination and preserving synapses. Without wishing to be bound by any theory, DPN may have a neuroprotective effect on oligodendrocytes and microglial/dendritic cells in the CNS. ERβ ligands can also play an important role in non-disease conditions with respect to synaptic plasticity, improving cognition and brain development.

However, DPN has a 70:1 specificity for ERβ over ERα, which can result in the development of undesirable off-target effects as seen with estriol. Doses needed to ameliorate EAE in mice are relatively high. One factor that influences the efficacious drug concentration level in a subject is the drug's poor penetration of the blood-brain barrier (BBB). ERβ ligands act in the brain and spinal cord tissue. Thus, provided herein are compounds and methods that increase the BBB penetration of DPN. In certain embodiments, the compounds provided herein are more lipophilic prodrug derivatives of DPN that liberate the active DPN at therapeutic concentrations in the central nervous system (CNS).

Disclosed herein are methods of treating a neurodegenerative disease comprising administering an ERβ ligand to a subject in need thereof.

In certain embodiments, the ERβ ligand is a compound of Formula (I)

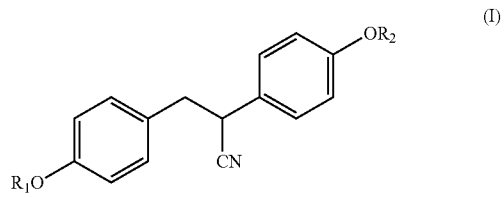

wherein $R_1$ and $R_2$ are each independently selected from —C(O)—$R_3$; and $R_3$ is selected from alkyl, alkoxy, alkoxyalkyl, aryloxyalkyl, cycloalkyl, cycloalkylalkyl, aryl, aralkyl, heterocyclyl, heterocyclylalkyl, heteroaryl, and heteroarylalkyl. In certain embodiments, the carbon bearing the CN substituent is in the R-configuration. In other embodiments, the carbon bearing the CN substituent is in the S-configuration.

In certain preferred embodiments, each $R_3$ is selected from alkyl, aryl and aralkyl. In some embodiments, each $R_3$ is selected from methyl, ethyl, isopropyl, t-butyl, substituted or unsubstituted phenyl, and substituted or unsubstituted benzyl.

In certain embodiments, the compound of Formula (I) is Compound 1:

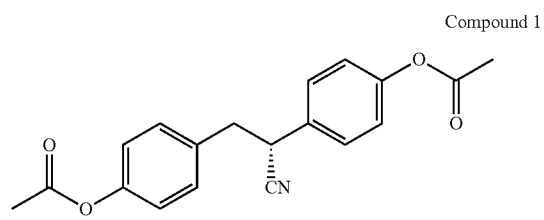 [SMILES: CC(=O)Oc1ccc(C[C@@H](C#N)c2ccc(OC(C)=O)cc2)cc1]

In certain embodiments, the compound of Formula (I) is Compound 2:

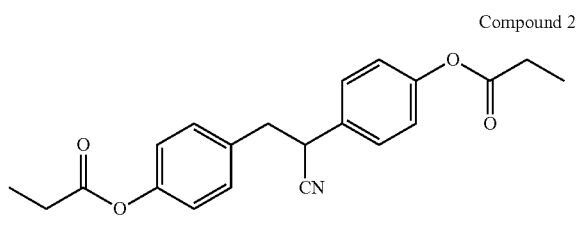 [SMILES: CCC(=O)Oc1ccc(CC(C#N)c2ccc(OC(=O)CC)cc2)cc1]

In certain embodiments, the compound of Formula (I) is Compound 3:

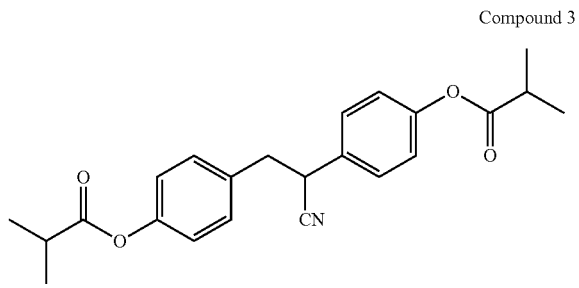 [SMILES: CC(C)C(=O)Oc1ccc(CC(C#N)c2ccc(OC(=O)C(C)C)cc2)cc1]

In certain embodiments, the compound of Formula (I) is Compound 4:

Compound 4

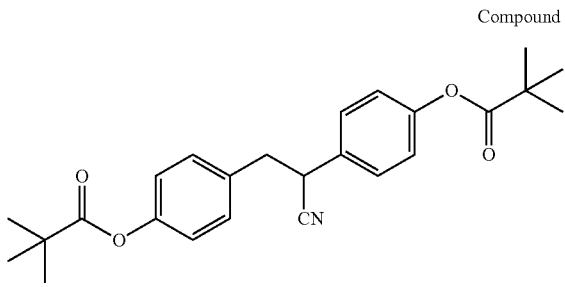

In certain embodiments, the compound of Formula (I) is Compound 5:

Compound 5

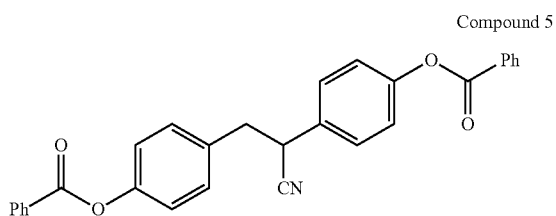 [SMILES: N#CC(Cc1ccc(OC(=O)c2ccccc2)cc1)c1ccc(OC(=O)c2ccccc2)cc1]

In certain embodiments, the compound of Formula (I) is Compound 6:

Compound 6

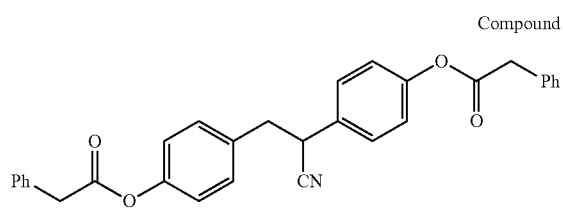

In certain embodiments, disclosed compounds can be the R-enantiomer at the cyano-substituent stereocenter. In other embodiments, disclosed compounds can be the S-enantiomer at the cyano-substituent stereocenter. In some embodiments, disclosed compounds can be a racemate having both enantiomers present.

In certain embodiments, compounds of Formula (I) act as prodrugs of DPN, which cross the BBB and then deliver DPN to brain and spinal cord tissue via hydrolysis of the phenol ester groups by an esterase. In certain embodiments, compounds of Formula (I) can be effective when administered (e.g., orally) at lower doses than a similarly effective dose of DPN.

In certain embodiments, the neurodegenerative disease is multiple sclerosis, such as relapsing-remitting multiple sclerosis, primary-progressive multiple sclerosis, secondary-progressive multiple sclerosis, or progressive-relapsing multiple sclerosis.

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. Exemplary substituted alkyl groups include, but are not limited to, acylaminoalkyl, alkoxyalkyl, aryloxyalkyl, cycloalkylalkyl, aralkyl, heterocyclylalkyl, and heteroarylalkyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The terms "amine" and "amino" are art-recognized and refer to both unsubstituted and substituted amines and salts thereof, e.g., a moiety that can be represented by

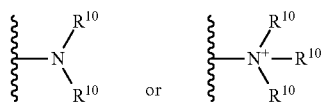

wherein each $R^{10}$ independently represents a hydrogen or a hydrocarbyl group, or two $R^{10}$ are taken together with the N atom to which they are attached complete a heterocycle having from 4 to 8 atoms in the ring structure. The term "aminoalkyl", as used herein, refers to an alkyl group substituted with an amino group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents (in which case, for example, the atoms within the aryl group are not counted when counting the carbon atoms in the alkyl substituent).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

In certain embodiments, compounds of the invention may be racemic. In certain embodiments, compounds of the invention may be enriched in one enantiomer. For example, a compound of the invention may have greater than about 30% ee, about 40% ee, about 50% ee, about 60% ee, about 70% ee, about 80% ee, about 90% ee, or even about 95% or greater ee. In certain embodiments, compounds of the invention may have more than one stereocenter. In certain such embodiments, compounds of the invention may be enriched in one or more diastereomer. For example, a compound of the invention may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the subject of one or more of the disclosed compositions. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of Formula (I)). A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present invention.

An "effective amount", as used herein, refers to an amount that is sufficient to achieve a desired biological effect. A "therapeutically effective amount", as used herein refers to an amount that is sufficient to achieve a desired therapeutic effect. For example, a therapeutically effective amount can refer to an amount that is sufficient to improve at least one sign or symptom of MS.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others. In the treatment of MS, a response typically indicates a reduced score on a functional test, such as, but not limited to, the Paced Serial Addition Test (PASAT); symbol digit modalities test (SDMT); expanded disability status score (EDSS); multiple sclerosis functional composite (MSFC); 25-foot walk test; 9-hole peg test; low contrast visual acuity; MS Quality of Life; Modified Fatigue Impact Scale; Beck Depression Inventory; 7/24 Spatial Recall Test; Benton Forms F & G; Buschke Selective Reminding Test; Verbal Paired Associates; and Word List Generation.

Pharmaceutical Compositions and Administration

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration.

The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Dosing

Actual dosage levels of the active ingredients in the pharmaceutical compositions may be varied so as to obtain an amount of the active ingredient that is effective to achieve the desired therapeutic response for a particular subject, composition, and mode of administration, without being toxic to the subject.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within about one hour, about 12 hours, about 24 hours, about 36 hours, about 48 hours, about 72 hours, or about a week of one another. Thus, a subject who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of Formula (I)) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

Methods of Use

Disclosed herein are methods of treating a neurodegenerative disease or condition comprising administering a compound of Formula (I) or a pharmaceutically acceptable salt thereof. In certain embodiments, the compound of Formula (I) is an ERβ ligand. In certain embodiments, the compound of Formula (I) is a prodrug of DPN. In certain preferred embodiments, the compound of Formula (I) is Compound 1.

In certain embodiments, the neurodegenerative disease or condition is multiple sclerosis. In certain embodiments, the multiple sclerosis is relapsing-remitting multiple sclerosis. In certain embodiments, the multiple sclerosis is secondary-progressive multiple sclerosis. In certain embodiments, the multiple sclerosis is primary-progressive multiple sclerosis. In certain embodiments, the multiple sclerosis is progressive-relapsing multiple sclerosis. In certain embodiments, the subject has a mild form of any one of the foregoing subtypes of MS. In certain embodiments, the subject has a moderate form of any one of the foregoing subtypes of MS. In certain embodiments, the subject has an aggressive form of any one of the foregoing subtypes of MS.

In certain embodiments, the multiple sclerosis is, more accurately, so-called clinically isolated syndrome (CIS). An ERβ ligand can be used, in accordance with the invention, to prevent or delay the onset of relapsing-remitting MS in subjects having CIS.

The various methods disclosed herein can be methods for improving walking, vision, balance, cognition, fatigue, or other symptoms in a subject, such as a subject with multiple sclerosis, and/or methods for improving multiple sclerosis functional composite (MSFC), EDSS, or MSSS scores in a subject, such as a subject with multiple sclerosis. Thus, in certain embodiments, the methods of treatment disclosed herein include methods for stabilizing or improving disability in a subject, whereby the subject's disability score (as measured by either of these tests or another suitable test) after six months, one year, or two years of therapy is at least about 10%, at least about 25%, at least about 40%, at least about 50%, or even at least about 60% higher relative to a control subject not receiving the ERβ ligand therapy (but otherwise receiving the same treatment as the ERβ ligand-treated subject). Alternatively, the subject's disability score (as measured by either of these tests or another suitable test) after six months, one year, or two years of therapy is within about 2% or within about 5% of an earlier assessment, or at least about 2%, at least about 5%, at least about at least about 10%, at least about 25%, at least about 40%, at least about 50%, or even at least about 60% higher than the earlier assessment.

For example, progression of a walking disability can be tested using a walking test, e.g., assessing the subject's performance on a 25-foot walk test at different points in time, such as at 0 months (baseline), 6 months, 1 year, and 2 years. In certain embodiments, if there is documented worsening in walking (takes more seconds) by about 20 percent as compared to baseline (optionally if this worsening is confirmed on a subsequent walk test (e.g., 3 months later)), then the subject is deemed to have progressive worsening in walking. For such a subject not already receiving ERβ ligand therapy, the subject demonstrating the progressive walking disability commences treatment with an ERβ ligand. The walking test may be repeated (e.g., at 1 year and/or 2 years from the start of ERβ ligand treatment) to assess whether the ERβ ligand treatment slowed or halted any further worsening in walking performance, e.g., as measured by the walking test.

Improvements in cognition outcomes associated with MS therapy, whether slowing of cognitive decline, stabilization of cognitive decline, or improvement of cognitive function, can be assessed using the PASAT (e.g., PASAT 2 or PASAT 3) or SDMT test, or alternatively the MS-COG test (see Erlanger et al., *J Neuro Sci* 340: 123-129 (2014)). Thus, in certain embodiments, the methods of treatment disclosed herein include methods for stabilizing or improving cognition in a subject, whereby the subject's cognition outcome after one year of therapy is at least about 2%, at least about 5%, at least about 10%, at least about 25%, at least about 40%, at least about 50%, or even at least about 60% higher relative to a control subject not receiving the ERβ ligand therapy (but otherwise receiving the same treatment as the ERβ ligand subject), e.g., as measured by any of the preceding tests. Alternatively, the subject's cognition outcome after six months, one year, or two years of therapy may be within about 2% or within about 5% of an earlier assessment, or at least about 2%, at least about 5%, at least about 10%, at least about 25%, at least about 40%, at least about 50%, or even at least about 60% higher than the earlier assessment, e.g., as measured by any of the preceding tests at different times.

For example, a subject who scores below 50 on PASAT (and optionally if such low score is verified upon a second subsequent test, such as within one week to one month of the first) may be deemed to have cognitive disability. For such a subject not already receiving ERβ ligand therapy, the subject demonstrating the cognitive disability may commence treatment with an ERβ ligand. In certain embodiments, the cognitive test may be repeated (e.g., at about six months from the start of ERβ ligand treatment) to assess whether the ERβ ligand treatment slowed or halted any further worsening in cognitive performance, e.g., as measured by the PASAT test. In certain such embodiments, the subject's score may increase by at least 3 points over the course of six to twelve months of ERβ ligand therapy.

Although the methods disclosed throughout the specification and claims are useful for treating multiple sclerosis in its various forms and stages, these methods can also be applied the treatment of other neurodegenerative diseases, such as, by way of illustration, Alzheimer's disease, Mild Cognitive Impairment (MCI), cognitive impairment with menopause (of natural aging or surgical), Parkinson's disease, stroke, amyotrophic lateral sclerosis, cerebellar ataxia, frontotemporal dementia, prion disease, Huntington's Disease, cerebral ischemia, idiopathic Morbus Parkinson, Parkinson syndrome, Morbus Alzheimers, cerebral dementia syndrome, infection-induced neurodegeneration disorders (e.g., AIDS-encephalopathy, Creutzfeld-Jakob disease, encephalopathies induced by rubiola and herpes viruses and borrelioses), metabolic-toxic neurodegenerative disorders (such as hepatic-, alcoholic-, hypoxic-, hypo- or hyperglycemically-induced encephalopathies), encephalopathies induced by solvents or pharmaceuticals, degenerative retina disorders, trauma-induced brain damage, trauma-induced bone marrow damage, cerebral hyperexcitability symptoms, cerebral hyperexcitability states (e.g., of varying origin, such as after the addition of and/or withdrawal of medicaments, toxins, noxae and drugs), neurodegenerative syndromes of the peripheral nervous system, peripheral nerve injury, and spinal cord injury.

In certain embodiments, different compounds of the invention may be conjointly administered with one or more other compounds of the invention. Moreover, such combinations may be conjointly administered with other therapeutic agents, such as other agents suitable for the treatment of immunological or neurological diseases, such as the agents identified above. In certain embodiments, conjointly administering one or more additional chemotherapeutic agents with a compound of the invention provides a synergistic effect. In certain embodiments, conjointly administering one or more additional chemotherapeutics agents provides an additive effect.

While the various methods disclosed herein are typically efficacious when administered without additional therapeutics, in certain embodiments, any of these methods further includes the step of administering to the subject an immunotherapeutic agent, wherein the immunotherapeutic agent is not an ERβ ligand. That is, in certain embodiments the subject is administered, in addition to the ERβ ligand (or placebo), a second agent useful in the treatment of MS. Such agents useful in the treatment of MS are, in general, immunotherapeutic agents. At least in connection with MS, such agents are sometimes referred to as disease-modifying therapies or disease-modifying therapeutics (DMTs).

The term "immunotherapeutic agent" as used herein refers to a compound with an objectively measurable effect on at least one aspect of the immune system or an immune response. In certain embodiments, the immunotherapeutic agent is immunosuppressive, i.e., it exerts an objectively measurable inhibitory effect on at least one aspect of the immune system or an immune response. In certain embodiments, the immunotherapeutic agent is anti-inflammatory. In certain embodiments, the immunotherapeutic agent is a small molecule (molecular weight less than or equal to about 1.5 kDa) pharmaceutical compound or composition. In certain embodiments, the immunotherapeutic agent is a biological compound or composition, e.g., an antibody, peptide, nucleic acid, etc.

In certain embodiments, the immunotherapeutic agent is selected from dimethyl fumarate (Tecfidera®; BG-12, which may be administered in an amount from about 220 mg to about 260 mg per day, such as about 220 mg, about 240 mg, or about 260 mg per day), fingolimod (Gilenya®, which may be administered in an amount from about 0.25 mg to about 0.75 mg per day, such as about 0.25 mg, about 0.50 mg, or about 0.75 mg per day), glatiramer acetate (Copaxone®, for example "longer-lasting" 40 mg/ml or 20 mg/ml versions), interferon beta-1a (Avonex® or Rebif®), interferon beta-1b (Betaseron® or Extavia®), mitoxantrone (Novantrone®), natalizumab (Tysabri®), and teriflunomide (Aubagio®, which may be administered in an amount from about 7 mg to about 14 mg per day, such as about 7 mg, about 10 mg, or about 14 mg per day), mycophenolate mofetil, paclitaxel, cyclosporine, corticosteroids (e.g., prednisone, methylprenisolone), azathioprine, cyclophosphamide, methotrexate, cladribine, 4-aminopyridine, and tizanidine. In certain embodiments, the immunotherapeutic agent is selected from dimethyl fumarate (Tecfidera®; BG-12), fingolimod (Gilenya®), glatiramer acetate (Copaxone®), interferon beta-1a (Avonex® or Rebif®), interferon beta-1b (Betaseron® or Extavia®), mitoxantrone (Novantrone®), natalizumab (Tysabri®), and teriflunomide (Aubagio®).

In certain embodiments, the immunotherapeutic agent is dimethyl fumarate (Tecfidera®; BG-12). In certain embodiments, the immunotherapeutic agent is fingolimod (Gilenya®). In certain embodiments, the immunotherapeutic agent is glatiramer acetate (Copaxone®). In certain embodiments, the immunotherapeutic agent is interferon beta-1a (Avonex® or Rebif®). In certain embodiments, the immunotherapeutic agent is interferon beta-1b (Betaseron® or Extavia®). In certain embodiments, the immunotherapeutic agent is mitoxantrone (Novantrone®). In certain embodiments, the immunotherapeutic agent is natalizumab (Tysabri®). In certain embodiments, the immunotherapeutic agent is teriflunomide (Aubagio®).

In certain embodiments, the subject is already receiving a disease-modifying therapeutic. In this circumstance, the subject can continue to receive the disease-modifying therapeutic while taking the ERβ ligand. Significantly, however, the dose of the disease-modifying therapeutic may be decreased when used in combination with the ERβ ligand. For example, a current standard dose for glatiramer acetate (Copaxone®) is 40 mg subcutaneously (s.c.) three times a week, or 20 mg s.c. daily. In conjunction with an ERβ ligand in accordance with the invention, the dose for glatiramer acetate (Copaxone®) may be reduced by up to about 50 percent or more, e.g., to 20 mg s.c. three times a week.

As another example, a current standard dose for fingolimod (Gilenya®) is 0.5 mg by mouth (p.o.) daily. In conjunction with an ERβ ligand in accordance with the invention, the dose for fingolimod (Gilenya®) may be reduced by up to about 50 percent or more, e.g., to 0.25 mg p.o. daily.

As another example, a current standard dose for dimethyl fumarate (Tecfidera®) is 240 mg p.o. daily. In conjunction with an ERβ ligand in accordance with the invention, the dose for dimethyl fumarate (Tecfidera®) may be reduced by up to about 50 percent or more, e.g., to 120 mg p.o. daily.

As yet another example, a current standard dose for interferon beta-1a (Avonex® or Rebif®) is 30 µg intramuscularly (i.m.) weekly (Avonex®) or 44 µg s.c. three days a week (Rebif®). In conjunction with an ERβ ligand in accordance with the invention, the dose for Avonex® may be reduced to 15 µg i.m. weekly, and the dose for Rebif® may be reduced to 22 µg s.c. three days a week.

As yet another example, a current standard dose for interferon beta-1b (Betaseron® or Extavia®) is 0.25 mg s.c. every other day (Betaseron® or Extavia®). In conjunction with an ERβ ligand in accordance with the invention, the dose for interferon beta-1b (Betaseron® or Extavia®) may be reduced to 0.125 mg s.c. every other day.

In certain embodiments, the subject is receiving an immunotherapeutic agent and has cognitive disability. For example, if a subject scores below 50 on PASAT, and optionally if such low score is verified upon retest within about one week to one month, then the subject may be deemed to have cognitive disability. In accordance with the invention, this cognitive disability is treated with an ERβ ligand and, in certain embodiments, followed up with further retest e.g., about six months from the start of ERβ ligand treatment, such as to achieve an increase in test score of at least 3 points.

In certain embodiments, the subject is receiving an immunotherapeutic agent and has progressive walking disability. For example, the subject performs a 25 foot walk test, e.g., at 0 months (baseline), 6 months, 1 year, and/or 2 years. If there is documented worsening in walking (takes more seconds), e.g., by about 20 percent as compared to baseline, and this worsening is confirmed on a repeated walk test, e.g., about 3 months later, then the subject is deemed to have progressive worsening in walking. In accordance with the invention, this progressive walking disability is treated with an ERβ ligand and, in certain embodiments, followed up with repeat walking test, e.g., at about 1 year or about 2 years from the start of ERβ ligand treatment, such as to stabilize or halt any further worsening in walking times.

In certain embodiments, the subject is receiving an immunotherapeutic agent and experiencing a relapse or progression of the multiple sclerosis. For example, a subject may experience a relapse or progression while on a maintenance dose of a DMT. Such subject can then begin concurrent treatment with an ERβ ligand in accordance with any of the various methods disclosed herein, e.g., to reduce the frequency and/or severity of relapses or to slow progression of the disease (e.g., as determined by assessment of one or more of walking, vision, balance, cognition, or other symptoms of the condition, e.g., as measured according to the Expanded Disability Severity Scale (EDSS) and/or the multiple sclerosis functional composite (MSFC)). Thus, the various embodiments of the methods disclosed herein can be methods for improving walking, vision, balance, cognition, or other symptoms in a subject, such as a subject with multiple sclerosis, and/or methods for improving EDSS or MSFC scores in a subject, such as a subject with multiple sclerosis.

In certain embodiments, the subject is receiving an immunotherapeutic agent and experiencing a relapse of the multiple sclerosis. For example, a subject may experience a relapse while on a maintenance dose of a DMT. Such subject can then begin concurrent treatment with an ERβ ligand in accordance with a method of the present invention, e.g., to reduce the frequency and/or severity of relapses.

In certain embodiments, the subject is receiving an immunotherapeutic agent selected from interferon-beta 1a, interferon-beta 1b, glatiramer acetate, natalizumab, mitoxantrone, fingolimod, teriflunomide, and dimethyl fumarate during a ramp-up period for dose of the immunotherapeutic agent, e.g., the subject begins receiving the immunotherapeutic and the ERβ ligand therapy at the same time or at about the same time (such as for subjects who have not previously received treatments for their disease). Advantageously, an ERβ ligand induces a rapid onset of therapeutic effect on MS, while commonly an immunotherapeutic agent such as interferon-beta 1a, interferon-beta 1b, glatiramer acetate, natalizumab, mitoxantrone, fingolimod, teriflunomide, or dimethyl fumarate may take weeks to months to induce observable improvements on some or all symptoms.

In certain embodiments, the subject is receiving glatiramer acetate during a ramp-up period for dose of the glatiramer acetate. In other certain embodiments, the subject is not already receiving a disease-modifying therapeutic.

When a given dose of any agent involves administration of more than a single unit dose, e.g., four capsules of an ERβ ligand, the individual unit doses can be administered at essentially the same time, or they can be administered at different times on a given day, provided the entire daily dose is administered within a single day. For example, four capsules of an ERβ ligand can be taken together essentially once a day, or they may be taken two at a time twice a day, or they may be taken one at a time four times a day. Additional schedules are contemplated by the invention, again provided the entire daily dose is administered within a single day. While it may be preferable that the subject follow the same schedule from one day to the next, such is not required, once again provided the entire daily dose is administered within a single day.

Clinically, MS can be assessed and monitored using any of a number of structural (anatomical) and functional tests, including, without limitation: magnetic resonance imaging (MRI); Paced Serial Addition Test (PASAT); symbol digit modalities test (SDMT); expanded disability status score (EDSS); multiple sclerosis functional composite (MSFC); 25-foot walk test; 9-hole peg test; low contrast visual acuity; MS Quality of Life; Modified Fatigue Impact Scale; Beck Depression Inventory; 7/24 Spatial Recall Test; Benton Forms F & G; Buschke Selective Reminding Test; Verbal Paired Associates; Word List Generation. Recently, the PASAT test of cognitive function has come under criticism by some for its test-retest reliability and practice effect whereby one naturally improves over time with repeated test taking. Polman C H et al., Neurology 74 Suppl 3: S8-15 (2010).

In some embodiments, assessment of MacDonald dissemination in space and time finds use in the present methods. For example, for dissemination in space, lesion imaging, such as, by way of illustration, Barkhof-Tintore MR imaging criteria, may be used. For instance, the following criteria can be evaluated: (1) at least one gadolinium-enhancing lesion or 9 T2 hyperintense lesions; (2) at least one infratentorial lesion; (3) at least one juxtacortical lesion; (4) at least 3 periventricular lesions; and (5) a spinal cord lesion. Such imaging criteria can optionally be used in combination with evaluation for immunoglobulin abnormalities in the cerebrospinal fluid (CSF), for example. For dissemination in time, MR imaging can also be used. For example, if an MR imaging scan of the brain performed at ≥3 months after an initial clinical event demonstrates a new gadolinium-enhancing lesion, this may indicate a new CNS inflammatory event, because the duration of gadolinium enhancement in MS is usually less than 6 weeks. If there are no gadolinium-enhancing lesions but a new T2 lesion (presuming an MR imaging at the time of the initial event), a repeat MR imaging scan after another 3 months may be needed with demonstration of a new T2 lesion or gadolinium-enhancing lesion. In various embodiments, any one or more of these structural (anatomical) and functional tests may be used in conjunction with the present invention (e.g., to assess the effectiveness of a disclosed treatment method).

In some aspects, the invention relates to a method of slowing, halting, or reversing physical disability or stabilizing or improving physical disability in a subject who has multiple sclerosis, comprising administering to the subject an ERβ ligand and a secondary agent. The ERβ ligand may be administered orally. The ERβ ligand may be formulated as a pill, e.g., for oral administration. The ERβ ligand may be administered orally in a dose equal or equivalent to about 8 mg of DPN per day. In certain embodiments, the ERβ ligand dose can range from about 5 mg to about 120 mg per day, such as about 10 mg to about 80 mg per day, such as about 30 mg to about 100 mg per day, such as about 50 mg to about 80 mg per day, such as about 5 mg to about 30 mg per day, and further such as about 7 mg to about 20 mg per day. In some embodiments, the DPN dose is about 60 mg per day. The ERβ ligand may be DPN or Compound 1. Physical disability may be assessed, for example, using the expanded disability status scale ("EDSS"). The subject may have relapsing-remitting multiple sclerosis or secondary progressive multiple sclerosis. For example, the subject may have secondary progressive multiple sclerosis and the ERβ ligand may be administered as a neuroprotective agent. The secondary agent may be glatiramer acetate copolymer 1. Glatiramer acetate copolymer 1 may be administered, for example, by injection. The ERβ ligand and secondary agent may be administered for at least about 12 months, such as for about 12 months, about 13 months, about 14 months, about 15 months, about 16 months, about 17 months, about 18 months, about 19 months, about 20 months, about 21 months, about 22 months, about 23 months, or about 24 months. The ERβ ligand and secondary agent may be administered for at least 24 months.

The method may further comprise evaluating the physical disability of a subject, e.g., by obtaining an EDSS score. The method may further comprise evaluating a change in the physical disability of a subject, e.g., by obtaining a first EDSS score, obtaining a second EDSS score, and comparing the first EDSS score and the second EDSS score, thereby evaluating the change in physical disability. The first EDSS score may be obtained prior to administering the ERβ ligand and the secondary agent, such as within a day, week, or month prior to administering the ERβ ligand and the secondary agent. The second EDSS score may be obtained a period of time after first administering the ERβ ligand and the secondary agent, such as at least 12 months after first administering the ERβ ligand and the secondary agent, such as about 12 months or about 24 months after first administering the ERβ ligand and the secondary agent.

In some embodiments, the invention relates to a method of slowing, halting, or reversing cognitive decline or stabilizing or improving cognitive function in a subject who has multiple sclerosis, comprising administering to the subject an ERβ ligand and a secondary agent. The ERβ ligand may be administered orally. The ERβ ligand may be formulated as a pill, e.g., for oral administration. The ERβ ligand may be administered orally in a dose equal or equivalent to about 8 mg of DPN per day. The ERβ ligand may be DPN or Compound 1. Cognitive function and or cognitive decline may be assessed, for example, using the paced auditory serial additional test ("PASAT"). The subject may have relapsing-remitting multiple sclerosis or secondary progressive multiple sclerosis. For example, the subject may have secondary progressive multiple sclerosis and the ERβ ligand may be administered as a neuroprotective agent. The secondary agent may be glatiramer acetate copolymer 1. Glatiramer acetate copolymer 1 may be administered, for example, by injection. The ERβ ligand and secondary agent may be administered for at least about 12 months, such as for about 12 months, about 13 months, about 14 months, about 15 months, about 16 months, about 17 months, about 18 months, about 19 months, about 20 months, about 21 months, about 22 months, about 23 months, or about 24 months. The ERβ ligand and secondary agent may be administered for at least about 24 months.

The method may further comprise evaluating the cognitive function of a subject, e.g., by obtaining a PASAT score. The method may further comprise evaluating a change in the cognitive function of a subject, e.g., by obtaining a first PASAT score, obtaining a second PASAT score, and comparing the first PASAT score and the second PASAT score, thereby evaluating the change in cognitive function. The first PASAT score may be obtained prior to administering the ERβ ligand and the secondary agent, such as within a day, week, or month prior to administering the ERβ ligand and the secondary agent. The second PASAT score may be obtained a period of time after first administering the ERβ ligand and the secondary agent, such as at least 12 months after first administering the ERβ ligand and the secondary agent, such as 12 months or 24 months after first administering the ERβ ligand and the secondary agent.

In some embodiments, the invention relates to a method of treating a human subject exhibiting at least one clinical sign or symptom of multiple sclerosis (e.g., weakness, numbness, tingling, loss of vision, memory difficulty, extreme fatigue, gadolinium enhancing lesions, the accumulation of T2 lesions, elevated Th1 cytokines (e.g., interferon gamma), and/or reduced Th2 cytokines (e.g., IL-10)), comprising administering to the subject an ERβ ligand (e.g., a compound of Formula I) and an immunomodulatory compound. The method may ameliorate the at least one sign or symptom of multiple sclerosis. The ERβ ligand may be Compound 1. The ERβ ligand may be administered orally at a dose of about 1 mg to about 20 mg per day, such as about 4 mg to about 16 mg. For example, the ERβ ligand may be administered orally at a dose of about 2 mg, about 4 mg, about 6 mg, about 8 mg, about 10 mg, about 12 mg, about 14 mg, or about 16 mg per day. The ERβ ligand may be administered at a dose sufficient to increase the serum concentration of the ERβ ligand in the subject to between about 2 ng/mL and about 30 ng/mL. In some embodiments, the dose is sufficient to increase the serum concentration of the ERβ ligand at about 6 ng/mL. In other embodiments, the serum concentration of the ERβ ligand is about 400 ng/mL to about 1000 ng/mL.

The immunomodulatory compound may be administered orally. The immunomodulatory compound may be, for example, fingolimod, teriflunomide, dimethyl fumarate, or a combination thereof. For example, the immunomodulatory compound may be fingolimod, and fingolimod may be administered at a dose of about 0.25 mg to about 0.75 mg per day, such as about 0.25 mg, about 0.5 mg, or about 0.75 mg per day. In some embodiments, fingolimod is administered daily. The immunomodulatory compound may be teriflunomide, and teriflunomide may be administered at a dose of about 7 mg to about 14 mg per day, such as about 7 mg, about 10 mg, or about 14 mg per day. In some embodiments, teriflunomide is administered daily. The immunomodulatory compound may be dimethyl fumarate, and dimethyl fumarate may be administered at a dose of about 220 mg to about 260 mg per day, such as about 220 mg, about 240 mg, or about 260 mg per day. In some embodiments, dimethyl fumarate is administered twice daily.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

EXAMPLES

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions with art-recognized alternatives and using no more than routine experimentation, are within the scope of the present application.

The following examples are put forth so as to provide those of ordinary skill in the art with a complete disclosure and description of how to make and use the methods of the invention, and are not intended to limit the scope of what the inventor(s) regard(s) as the invention.

Unless noted otherwise, the starting materials for the experiments described herein were obtained from commercial sources or known procedures and were used without further modification.

Exemplary Synthesis

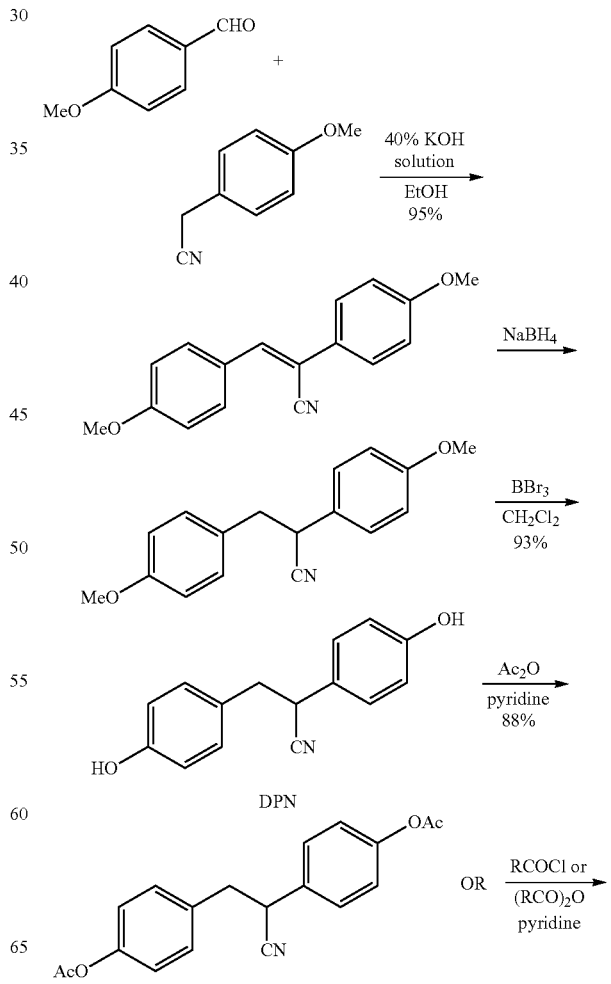

-continued

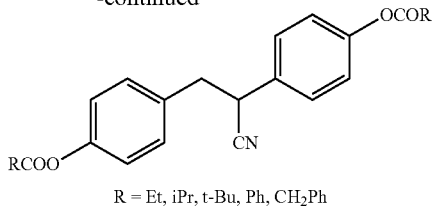

R = Et, iPr, t-Bu, Ph, CH$_2$Ph

In the first step, formation of the substituted stilbene occurred through basic addition of 2-(4-methoxyphenyl)acetonitrile to 4-methoxybenzaldehyde in high yield. Reduction of the stilbene using NaBH$_4$ to afford 2,3-bis(4-methoxyphenyl)propanenitrile was followed by treatment with BBr$_3$ to cleave the methyl ethers, giving DPN in high yield.

DPN was then acetylated using acetic anhydride to provide Compound 1. Either the corresponding anhydride or acyl chloride was used to provide Compounds 2-6.

For an exemplary synthesis of the R-enantiomer of DPN, see Carroll, V M. et al., *J. Med. Chem.* 2012 55:528-537.

Example 1: Administration of Compound 1 to Mice with Active EAE 8-10 weeks old C57BL6 female mice were induced with active EAE and divided into 5 groups for treatment; Vehicle (placebo—negative control), DPN high dose (positive control), DPN low dose (positive control), Compound 1 high dose (test) and Compound 1 low dose (test). Active EAE was induced by subcutaneous injections of myelin oligodendrocyte glycoprotein (MOG peptide 35-55) emulsified in complete freund's adjuvant supplemented with *Mycobacterium tuberculosis* near inguinal and auxiliary lymph nodes at Day 0 and Day 7 of induction with standard pertussis toxin given by intraperitoneal injections at Day 0 and Day 2.

The treatment of DPN and Compound 1 started at Day 12 of EAE (2 days after onset of clinical disease) and animals were dosed every other day. The high doses of DPN and Compound 1 were each 1.34 µM (8 mg/kg for DPN and 10.8 mg/kg for Compound 1). The low doses of DPN and Compound 1 were each 0.33 µM (2 mg/kg for DPN and 2.7 mg/kg for Compound 1). This dosing regimen of dosing every two days had been shown in the past with generic DPN to be tolerable in chronic experiments and also to be efficacious in EAE. Treatment continued every other day from onset of disease at day 12 until the end of the study at day 48. FIG. 1A depicts the increase in EAE clinical score for mice given vehicle, DPN or Compound 1. Both DPN and Compound 1 have protective effects on EAE disease progression at the high dose (DPN vs Vehicle; p=0.1330, Compound 1 vs Vehicle; p=00164). There was no disease improvement in the vehicle group, whereas both DPN and Compound 1 treated mice showed improvement in maintaining effective amounts of DPN in plasma (FIG. 1B), spinal cord tissue (FIG. 1C) and brain tissue (FIG. 1D) three hours after the end of disease. These results indicated that Compound 1 has similar protective effects as compared to DPN on EAE clinical disease when used at high doses.

Example 2: Administration of Compound 1 to Mice with Adoptive EAE

Active EAE induction in Example 1 uses pertussis toxin to artificially make the BBB more permeable and permit more infiltration of activated Th1/Th17 immune cells into the CNS. However, an EAE model that artificially opens the BBB may not be optimal to show differences between DPN and Compound 1 if differences are mediated by being more lipophilic to enable better crossing of the BBB. Thus, an alternative EAE induction method was used. Adoptive EAE uses MOG primed and activated immune cells from donor immunized mice for subsequent transfer into recipient mice with no administration of pertussis toxin. Thus, the blood brain barrier interactions in adoptive EAE are more physiologic than in active EAE.

The experimental setup and monitoring were the same as in Example 1, except in adoptive EAE, DPN and Compound 1 treatments were given to mice that were recipients of donor immune cells for disease induction. In addition to repeating the above (8 mg/kg/day) dose for treatment of DPN and Compound 1 in adoptive EAE, additional groups of mice were administered a lower 4-fold dose (2 mg/kg/day) for each drug. The lower dose was designed to differentiate the potency of DPN vs. Compound 1. This experiment was larger since 2 sets of mice (donors and recipients) were needed and 2 doses were used, making the adoptive EAE experiment 4 times larger than the active EAE experiment 1.

FIG. 2A shows the EAE clinical score to assess walking ability for each cohort of mice as in FIG. 1 (with higher scores indicating worse walking). Compound 1 and DPN showed dose responses and more efficacy with Compound 1 as compared to DPN in adoptive EAE. Plasma concentrations of DPN were measured 24 hours after dosing as shown in FIG. 2B and there was no difference between Compound 1 vs DPN at this late time point. Brain and spinal cord levels were undetectable 24 hours after dosing.

FIGS. 3C, 3D, 3E and 3F illustrate the EAE clinical scores of each of the 4 mouse cohorts, showing the increase efficacy of Compound 1 vs. DPN. FIG. 3A is a graph of EAE clinical score during days of treatment with vehicle and DPN at high and low doses. FIG. 3B is a graph of EAE clinical score during days of treatment with vehicle and Compound 1 at high and low doses. FIG. 3C is a graph of EAE clinical score during days of treatment with vehicle and both DPN and Compound 1 at the high dose. FIG. 3D is a graph of EAE clinical score during days of treatment with both DPN and Compound 1 at the high dose.

Example 3: Tissue Concentrations of DPN and Compound 1 in Healthy Mice

In this experiment, plasma, brain and spinal cord concentrations of DPN were assessed. However, instead of using mg/kg equivalence between DPN and Compound 1 as in Examples 1 and 2, here doses in molar equivalence were used (1.34 µM high dose and 0.33 µM low dose). Healthy mice (n=3 in each group) were dosed with Compound 1 or DPN, then tissues were sacrificed at 15 minutes, 3 hours, 6 hours and 12 hours. The levels of DPN were measured in each tissue at each time point during dosing with either generic DPN or Compound 1. Compound 1 levels were not measured. Despite dosing with molar equivalents, levels of DPN in tissues during dosing with Compound 1, as compared to DPN, were initially (at 15 minutes) lower with Compound 1, as compared to DPN, in the plasma, brain and spinal cord. However, at 3 and 6 hours, levels were higher with Compound 1, as compared to DPN, in all three tissues. At 12 hours, only high dose Compound 1 was detectable in plasma. FIGS. 4A, 4B and 4C show the DPN and Compound 1 concentrations over time in plasma (FIG. 4A), brain tissue (FIG. 4B), and spinal cord tissue (FIG. 4C).

Figure 5A:
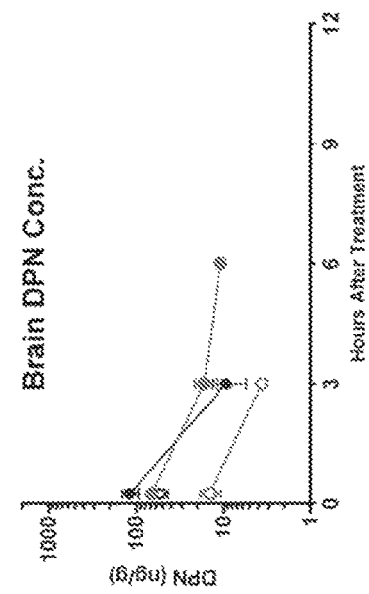
FIG. 5A shows that Compound 1 at the high dose resulted in a higher level of DPN in plasma that persisted at 12 hours after end of disease.
Figure 5B:
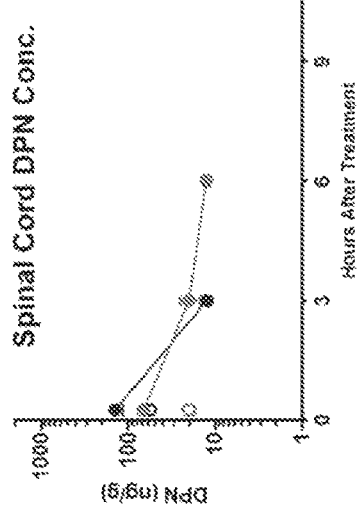
FIG. 5B shows that Compound 1 at the high dose provided a DPN concentration in spinal cord tissue that persisted at 6 hours after end of disease.
Figure 5C:
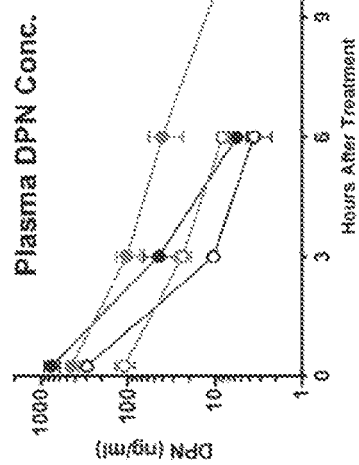
FIG. 5C shows that Compound 1 at the high dose provided a DPN concentration in brain tissue that persisted at 6 hours after end of disease.

This experiment was repeated and the data above was confirmed. FIG. 5A shows that Compound 1 at the high dose resulted in a higher level of DPN in plasma that persisted at 12 hours after end of disease. FIG. 5B shows that Compound 1 at the high dose provided a DPN concentration in spinal cord tissue that persisted at 6 hours after end of disease. FIG. 5C shows that Compound 1 at the high dose provided a DPN concentration in brain tissue that persisted at 6 hours after end of disease.

Figure 6C:
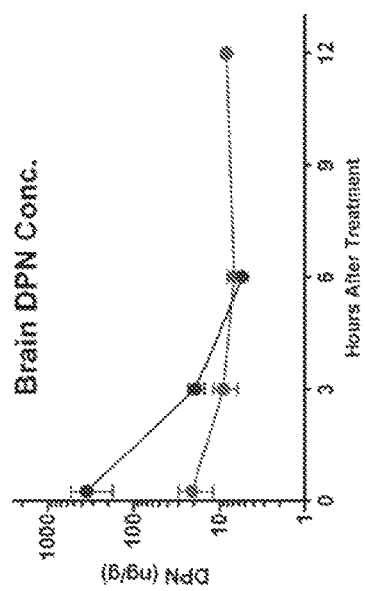
FIG. 6C shows that Compound 1 at the high dose provided a DPN concentration in brain tissue that persisted at 12 hours after end of disease.
Figure 6B:
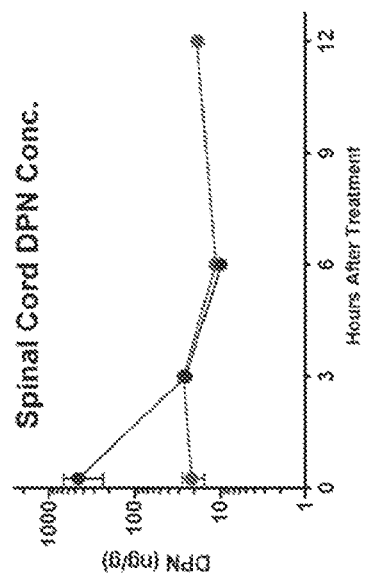
FIG. 6B shows that Compound 1 at the high dose provided a DPN concentration in spinal cord tissue that persisted at 12 hours after end of disease.
Figure 6A:
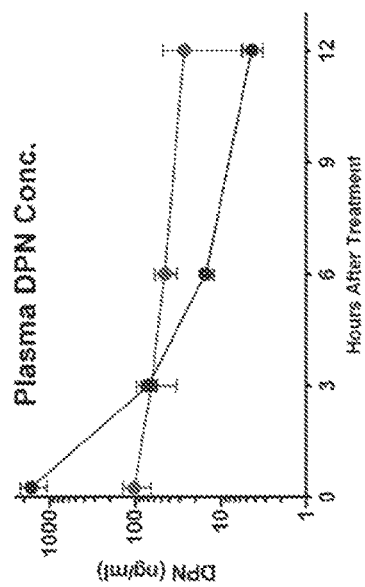
FIG. 6A shows that Compound 1 at the high dose resulted in a higher level of DPN in plasma that persisted at 12 hours after end of disease.

This experiment was repeated with fresher standards and faster freezing of tissues once obtained from the mouse sacrifice. Only the high dose of DPN and Compound 1 were repeated. FIG. 6A shows that Compound 1 at the high dose resulted in a higher level of DPN in plasma that persisted at 12 hours after end of disease. FIG. 6B shows that Compound 1 at the high dose provided a DPN concentration in spinal cord tissue that persisted at 6 hours after end of disease. FIG. 6C shows that Compound 1 at the high dose provided a DPN concentration in brain tissue that persisted at 6 hours after end of disease.

Without wishing to be bound by any theory, Compound 1 could be acting as a more lipophilic prodrug of DPN where its hydrolysis rate to give DPN allows for measurable concentrations of DPN over a longer time period.

Example 4: Administration of Compounds 1 and 2 to Mice with Adoptive EAE

The experimental setup and monitoring was the same as in Example 2. FIGS. 7A, 7B and 7C show the DPN, Compound 1, and Compound 2 concentrations over time in plasma (FIG. 7A), spinal cord tissue (FIG. 7B), and brain tissue (FIG. 7C). In the first 6 hours after treatment, Compound 2 had the highest concentration in plasma, spinal cord and brain tissue, illustrating its higher tissue penetration and stability in liquid and solid tissues. Both Compounds 1 and 2 persisted in brain and spinal tissue at 12 hours. Without wishing to be bound by any theory, the more lipophilic ester groups on Compound 2 may contribute to increased blood-brain permeability and slower hydrolysis to provide measurable amounts of DPN over time.

The invention claimed is:

1. A method of treating multiple sclerosis, comprising orally administering an ERβ ligand to a subject in need thereof wherein the ERβ ligand is a compound of Formula (I)

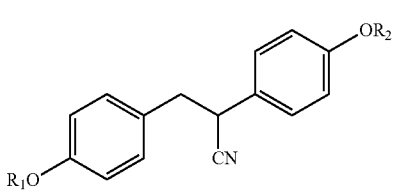

wherein
$R_1$ and $R_2$ are each independently —C(O)—$R_3$; and
each $R_3$ is independently selected from alkyl, alkoxy, alkoxyalkyl, aryloxyalkyl, cycloalkyl, cycloalkylalkyl, aryl, aralkyl, heterocyclyl, heterocyclylalkyl, heteroaryl, and heteroarylalkyl.

2. The method of claim 1, wherein $R_3$ is selected from alkyl, aryl and aralkyl.

3. The method of claim 2, wherein $R_3$ is selected from methyl, ethyl, isopropyl, t-butyl, phenyl and benzyl.

4. The method of claim 1, wherein the carbon bearing the CN substituent is in the R-configuration or the S-configuration.

5. The method of claim 1, wherein the ERβ ligand is Compound 1:

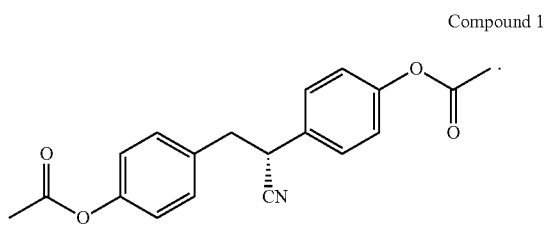 [SMILES: CC(=O)Oc1ccc(C[C@@H](C#N)c2ccc(OC(C)=O)cc2)cc1]

Compound 1

6. The method of claim 1, wherein the ERβ ligand is selected from:

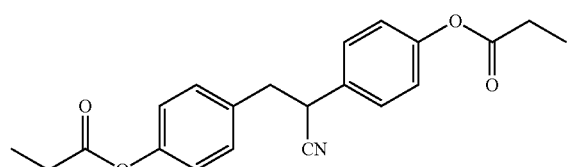

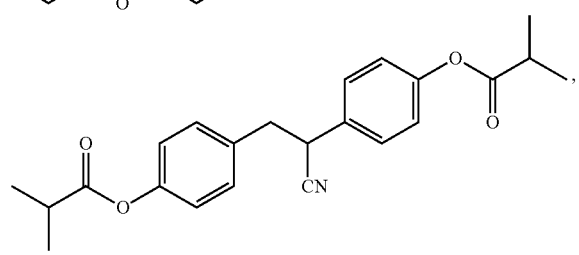

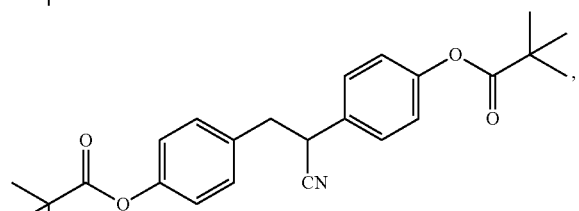

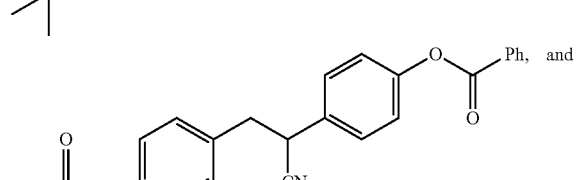

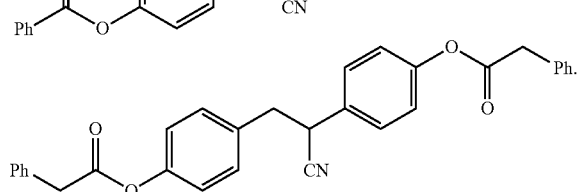

7. The method of claim 1, wherein the multiple sclerosis is relapsing-remitting multiple sclerosis.

8. The method of claim 1, wherein the multiple sclerosis is secondary-progressive multiple sclerosis.

9. The method of claim 1, wherein the multiple sclerosis is primary-progressive multiple sclerosis.

10. The method of claim 1, wherein the multiple sclerosis is progressive-relapsing multiple sclerosis.

11. The method of claim 1, wherein the multiple sclerosis is clinically isolated syndrome (CIS).

12. The method of claim 1, wherein the ERβ ligand is administered orally.

13. The method of claim 1, wherein the subject is not being treated with an immunotherapeutic agent.

14. The method of claim 1, further comprising conjointly administering to the subject an immunotherapeutic agent.

15. The method of claim 14, wherein treatment with the immunotherapeutic agent is initiated at the same time or about the same time as initiation of treatment with the ERβ ligand.

16. The method of claim 14, wherein the immunotherapeutic agent is selected from interferon-beta 1a, interferon-beta 1b, glatiramer acetate, natalizumab, mitoxantrone, fingolimod, teriflunomide, dimethyl fumarate, mycophenolate mofetil, paclitaxel, cyclosporine, corticosteroids, azathioprine, cyclophosphamide, methotrexate, cladribine, 4-aminopyridine, and tizanidine.

17. The method of claim 14, wherein the amount of the immunotherapeutic agent administered in combination with the ERβ ligand is less than a therapeutically effective amount when the immunotherapeutic agent is administered alone.

18. The method of claim 1, wherein the ERβ ligand is administered at a dose of about 5 mg to about 120 mg per day.

19. The method of claim 14, wherein the immunotherapeutic agent is glatiramer acetate.

* * * * *